(12) United States Patent
Majolagbe

(10) Patent No.: US 11,147,661 B2
(45) Date of Patent: Oct. 19, 2021

(54) KINK RESISTANT GRAFT

(71) Applicant: W. L. Gore & Associates, Inc., Newark, DE (US)

(72) Inventor: Kehinde A. Majolagbe, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 299 days.

(21) Appl. No.: 15/671,883

(22) Filed: Aug. 8, 2017

(65) Prior Publication Data

US 2018/0036112 A1 Feb. 8, 2018

Related U.S. Application Data

(60) Provisional application No. 62/372,031, filed on Aug. 8, 2016.

(51) Int. Cl.
*A61F 2/07* (2013.01)
*A61F 2/00* (2006.01)

(52) U.S. Cl.
CPC .............. *A61F 2/07* (2013.01); *A61F 2/0077* (2013.01); *A61F 2002/0081* (2013.01); *A61F 2210/0014* (2013.01); *A61F 2210/0057* (2013.01); *A61F 2210/0076* (2013.01); *A61F 2240/001* (2013.01); *A61F 2250/0026* (2013.01); *A61F 2250/0029* (2013.01); *A61F 2250/0037* (2013.01); *A61F 2250/0069* (2013.01)

(58) Field of Classification Search
CPC ........ A61F 2/06; A61F 2/07; A61F 2002/072; A61F 2002/075; A61F 2210/0057; A61F 2210/0076; A61F 2250/0007
See application file for complete search history.

(56) References Cited

U.S. PATENT DOCUMENTS

| | | | |
|---|---|---|---|
| 4,892,539 A * | 1/1990 | Koch | A61F 2/06 139/387 R |
| 5,084,065 A | 1/1992 | Weldon | |
| 5,108,424 A | 4/1992 | Hoffman, Jr. | |
| 5,341,849 A | 8/1994 | Mang | |
| 5,476,506 A * | 12/1995 | Lunn | A61F 2/06 623/1.13 |
| 5,573,039 A | 11/1996 | Mang | |
| 6,358,275 B1 | 3/2002 | McLlroy et al. | |
| 6,673,102 B1 | 1/2004 | Vonesh et al. | |

(Continued)

FOREIGN PATENT DOCUMENTS

| | | |
|---|---|---|
| CN | 102202608 A | 9/2011 |
| EP | 1734070 A1 | 12/2006 |

(Continued)

OTHER PUBLICATIONS

International Search Report and Written Opinion from PCT/US2017/045936, dated Oct. 24, 2017, 9 pages.

*Primary Examiner* — Ryan J. Severson

(57) ABSTRACT

A kink resistant stent graft includes a graft forming a tube with a central lumen extending from a first end of the tube to a second end of the tube and a stent secured to the graft adjacent the first end of the tube. The graft includes a corrugated inner graft layer forming at least a middle portion of the tube, and an outer graft layer covering the corrugated inner graft layer.

20 Claims, 3 Drawing Sheets

(56) References Cited

U.S. PATENT DOCUMENTS

| | | | | |
|---|---|---|---|---|
| 7,318,835 B2* | 1/2008 | Berra | ............... | A61F 2/06 623/1.12 |
| 7,510,571 B2* | 3/2009 | Spiridigliozzi | ............ | A61F 2/06 623/1.13 |
| 8,066,758 B2 | 11/2011 | Bogert | | |
| 8,313,524 B2 | 11/2012 | Edwin et al. | | |
| 8,491,649 B2* | 7/2013 | Mach | ............... | A61F 2/07 623/1.28 |
| 8,579,961 B2* | 11/2013 | Casey, II | ............... | A61F 2/06 623/1.13 |
| 8,652,284 B2* | 2/2014 | Bogert | ............... | A61F 2/06 156/172 |
| 9,044,311 B2* | 6/2015 | Rasmussen | ............... | A61F 2/06 |
| 9,107,741 B2* | 8/2015 | Bui | ............... | A61F 2/07 |
| 9,427,304 B2* | 8/2016 | Kariniemi | ............... | A61F 2/07 |
| 9,572,654 B2* | 2/2017 | Edwin | ............... | A61L 27/16 |
| 10,028,849 B2* | 7/2018 | Bui | ............... | A61F 2/07 |
| 10,098,772 B2* | 10/2018 | Lerdahl | ............... | A61F 2/07 |
| 10,105,209 B2* | 10/2018 | Kerr | ............... | A61F 2/07 |
| 2003/0088305 A1* | 5/2003 | Van Schie | ............... | A61F 2/06 623/1.12 |
| 2004/0019375 A1* | 1/2004 | Casey, II | ............... | A61F 2/06 623/1.28 |
| 2004/0033364 A1 | 2/2004 | Spiridigliozzi et al. | | |
| 2007/0067014 A1* | 3/2007 | Ke | ............... | A61F 2/07 623/1.13 |
| 2007/0198079 A1 | 8/2007 | Casey et al. | | |
| 2008/0132993 A1* | 6/2008 | Rasmussen | ............... | A61F 2/06 623/1.13 |
| 2009/0099642 A1* | 4/2009 | Lerdahl | ............... | A61F 2/07 623/1.13 |
| 2009/0125095 A1* | 5/2009 | Bui | ............... | A61F 2/07 623/1.13 |
| 2009/0171451 A1* | 7/2009 | Kuppurathanam | ............... | A61F 2/07 623/1.36 |
| 2010/0106235 A1* | 4/2010 | Kariniemi | ............... | A61F 2/07 623/1.11 |
| 2013/0345729 A1 | 12/2013 | Li | | |
| 2015/0320578 A1* | 11/2015 | Bui | ............... | A61F 2/07 623/1.35 |
| 2017/0224468 A1* | 8/2017 | Kerr | ............... | A61F 2/07 |
| 2017/0224469 A1* | 8/2017 | Kerr | ............... | A61F 2/07 |
| 2018/0036112 A1* | 2/2018 | Majolagbe | ............... | A61F 2/0077 |
| 2018/0071078 A1* | 3/2018 | Majolagbe | ............... | A61F 2/07 |

FOREIGN PATENT DOCUMENTS

| | | |
|---|---|---|
| EP | 3496661 A1 | 6/2019 |
| JP | 08-033660 A | 2/1996 |
| JP | 2005-298554 A | 10/2005 |
| JP | 2005-530549 A | 10/2005 |
| JP | 2010-279490 A | 12/2010 |
| WO | 2002/100454 A1 | 12/2002 |
| WO | 2004/000375 A1 | 12/2003 |
| WO | WO-2006026725 | 3/2006 |
| WO | 2018/031565 A1 | 2/2018 |

* cited by examiner

KINK RESISTANT GRAFT

CROSS-REFERENCE TO RELATED APPLICATION

This application claims the benefit of U.S. Provisional Application 62/372,031, filed Aug. 8, 2016, which is herein incorporated by reference in its entirety.

TECHNICAL FIELD

The present disclosure relates generally to implantable prostheses, including implantable endoprostheses, such as grafts and stent grafts.

BACKGROUND

Aneurysms occur in blood vessels at sites where, due to age, disease or genetic predisposition of the patient, the strength or resilience of the vessel wall is insufficient to prevent ballooning or stretching of the wall as blood passes through. If the aneurysm is left untreated, the blood vessel wall may expand and rupture, often resulting in death.

To prevent rupturing of an aneurysm, a stent graft may be introduced into a blood vessel percutaneously and deployed to span the aneurysmal sac. Stent grafts include a graft fabric secured to a cylindrical scaffolding or framework of one or more stents. The stent(s) can help provide the outward radial force needed to create a seal between the graft and a healthy portion of the vessel wall and provide migration resistance. Blood flowing through the vessel can be channeled through the luminal surface of the stent graft to reduce, if not eliminate, the stress on the vessel wall at the location of the aneurysmal sac. Stent grafts may reduce the risk of rupture of the blood vessel wall at the aneurysmal site and allow blood to flow through the vessel without interruption.

Aneurysms occurring in the aorta, the largest artery in the human body, may occur in the chest (thoracic aortic aneurysm) or in the abdomen (abdominal aortic aneurysm). Due to the curvature of the aortic arch, thoracic aortic aneurysms can be particularly challenging to treat. Other parts of the vasculature, such as the common iliac artery which extends from the aorta, can also be tortuous. Hence, a stent graft deployed into such regions is preferably able to conform to the vasculature. A high degree of conformability can help allow the stent graft to bend and optimally appose and seal against the native vessel, for example.

SUMMARY

This disclosure is generally directed to kink resistant grafts including a corrugated graft layer including stored length by way of the corrugations and a second graft layer covering the corrugated graft layer. The expansion of the corrugations on the outside radius of a bend may allow such kink resistant grafts to resist kinking when implanted within a bent portion of a vasculature of a patient, such as the thoracic aorta.

In one variation, a kink resistant stent graft includes a graft forming a tube with a central lumen extending from a first end of the tube to a second end of the tube and a stent secured to the graft adjacent the first end of the tube. The graft includes a corrugated inner graft layer forming at least a middle portion of the tube, and an outer graft layer covering the corrugated inner graft layer.

In some examples, the corrugated inner graft layer extends from the first end of the tube to the second end of the tube. In some of such examples, the outer graft layer extends from the first end of the tube to the second end of the tube.

In the same or different examples, the corrugations provide a stored length of the corrugated inner graft layer of at least twenty-five percent.

In the same or different examples, the corrugations provide a stored length of the corrugated inner graft layer of at least fifty percent.

In the same or different examples, at least one of the corrugated inner graft layer and the outer graft layer are formed from expanded polytetrafluoroethylene (ePTFE) film.

In the same or different examples, the outer graft layer is formed from a stretchable film.

In the same or different examples, the corrugated inner graft layer and the outer graft layer are bonded to one another.

In the same or different examples, the graft is configured to resist kinking while experiencing a 90 degree bend with an internal fluid pressure of at least 100 mmHg in that the graft is configured to maintain at least 60% of its cross-sectional area at the apex of the 90 degree bend while experiencing the internal fluid pressure of at least 100 mmHg.

In the same or different examples, a middle portion of the tube between the first end and the second end is free of any stent, the middle portion having a length of at least twice an external diameter of the tube at the middle portion.

In the same or different examples, an internal diameter of the tube is at least 12 mm.

In the same or different examples, the stent is a self-expanding stent.

In the same or different examples, the stent is a first stent, the kink resistant stent graft further comprising a second stent secured to the graft adjacent the second end of the tube.

In another variation, a method of forming a kink resistant graft comprises wrapping a film to form an inner graft layer forming a tube with a central lumen extending from a first end of the tube to a second end of the tube, scrunching the inner graft layer to form corrugations in the inner graft layer, the corrugations providing a stored length of the corrugated inner graft layer of at least twenty-five percent, wrapping an outer graft layer over the corrugated inner graft layer to cover the corrugated inner graft layer, and bonding the outer graft layer to the corrugated inner graft layer to form the kink resistant graft.

In the same or different examples, the method further comprises, securing a stent to the graft adjacent the first end of the tube.

In some examples, wrapping the film to form the inner graft layer forming the tube includes wrapping more than one layer of the film to form the tube.

In the same or different examples, the method further comprises, after wrapping the film to form the inner graft layer forming the tube and before scrunching the inner graft layer to form the corrugations in the inner graft layer, heating the wrapped film to set the film in the tube.

In the same or different examples, the method further comprises, after wrapping the outer graft layer over the corrugated inner graft layer to cover the corrugated inner graft layer, bonding the wrapped outer graft layer to the corrugated inner graft layer.

In the same or different examples, the kink resistant graft is configured to resist kinking while experiencing a 90 degree bend with an internal fluid pressure of at least 100 mmHg in that the kink resistant graft is configured to maintain at least 60% of its cross-sectional area at the apex of the 90 degree bend while experiencing the internal fluid pressure of at least 100 mmHg.

In the same or different examples, the kink resistant graft has a wall thickness of no greater than 0.20 nm.

While multiple examples are disclosed, still other examples of the present invention will become apparent to those skilled in the art from the following detailed description, which shows and describes illustrative examples of the invention. Accordingly, the drawings and detailed description are to be regarded as illustrative in nature and not restrictive.

BRIEF DESCRIPTION OF THE DRAWINGS

The accompanying drawings are included to provide a further understanding of the disclosure and are incorporated in and constitute a part of this specification, illustrate examples of the disclosure, and together with the description serve to explain the principles of the disclosure, wherein.

DETAILED DESCRIPTION

Aneurysms that occur in areas of tortuous vascular anatomy may be difficult to repair using grafts or stent grafts. On one hand, the inclusion of stents along the length of a graft may resist kinking and help maintain the internal diameter of a stent graft experiencing a bend at the treatment site in accordance with the vascular anatomy at the treatment site. However, such stents may cause undesirable pressure on the wall of the vasculature. Stent elements closely located to each other along the length of a graft may further limit the bending radius of a stent graft in that adjacent stent elements may interfere with one another along an interior radius of the bend. Moreover, the absence of closely located stent elements along the length of a graft may result in the graft material kinking adjacent a bend. Furthermore, minimally invasive implantation techniques require tight compaction of the endoprosthesis during delivery to the treatment site. In various instances, stent elements of a stent graft may not be as compactable as graft material of the stent graft.

Figure 1A:
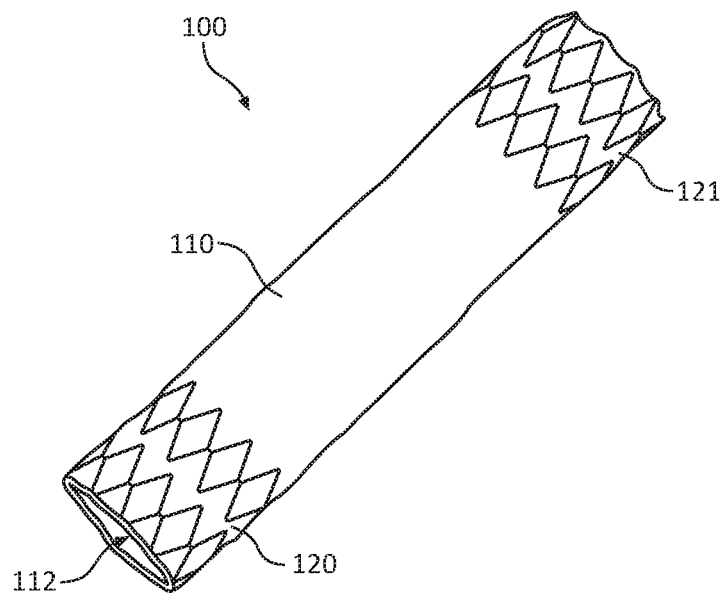
FIGS. 1A and 1B illustrate a kink resistant stent graft.
Figure 1B:
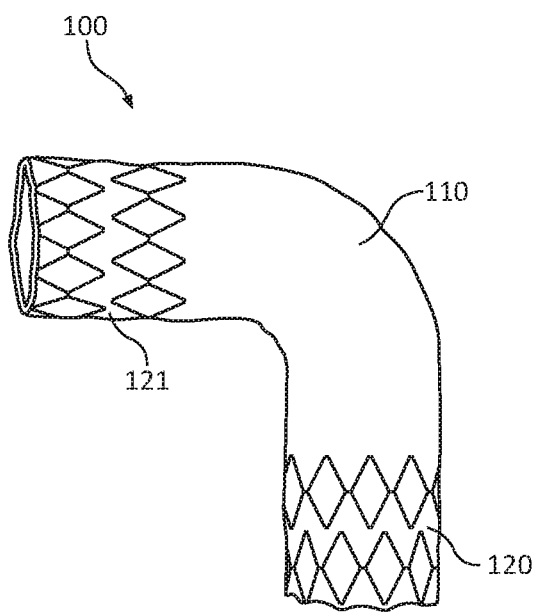

FIGS. 1A and 1B illustrate kink resistant stent graft 100. Stent graft 100 includes graft 110, which forms a tube with central lumen from a first end of the tube to a second end of the tube. As described in further detail with respect to FIGS. 2A-2E, stent graft 100 includes a corrugated inner graft layer 106 (FIG. 2C) forming at least a middle portion of the tube, and an outer graft layer 108 (FIG. 2D) covering the corrugated inner graft layer.

Corrugated inner graft layer 106 includes stored length by way of the corrugations, which can also be described as folds, creases, undulations, crinkles and the like. The expansion, or elongation of the corrugations on the outside radius of a bend, as shown in FIG. 1B allows stent graft 100 to resist kinking when implanted within a bent portion of a vasculature of a patient, such as the thoracic aorta. By resisting kinking the design of graft 110 may limit the need for stent elements within a middle portion of a graft 110, or other portion of the graft 110 corresponding to the corrugations. Stent graft 100 may conform to tortuous vascular anatomy without kinking, while also facilitating tight compaction for intravascular delivery to the treatment site. Although various examples are provided with a middle portion having corrugations, it should be understood that other examples include either end portion having corrugations or the middle portion being characterized by an absence of corrugations.

Moreover, potential materials for graft members include, for example, expanded polytetrafluoroethylene (ePTFE), polyester, polyurethane, fluoropolymers, such as perfouorelastomers and the like, polytetrafluoroethylene, silicones, urethanes, ultra-high molecular weight polyethylene, aramid fibers, and combinations thereof. Other examples for a graft member material can include high strength polymer fibers such as ultra-high molecular weight polyethylene fibers (e.g., Spectra®, Dyneema Purity®, etc.) or aramid fibers (e.g., Technora®, etc.).

In addition to graft 110, stent graft 100 further includes stent elements 120 secured to graft 110 adjacent a first end of the tube of graft 110, and stent elements 121 secured to graft 110 adjacent a second end of the tube. Stent elements 120, 121 may function to seal the exterior ends of stent graft 100 to an interior of a vessel wall in order to direct blood flow past an aneurism in a vessel wall. In various applications, a middle portion of the tube of graft 110 is free of any stent. In some examples this middle portion may have a length of at least twice an external diameter of the tube of graft 110 at the middle portion.

As shown, stent graft 100 includes two stent elements 120 and two stent elements 121. In other examples, stent elements 120 may include one or more than two stent elements, and stent elements 121 may include one or more than two stent elements. Furthermore, stent elements 121 are optional in that some examples may not include stent elements on both ends, e.g., such that stent elements are only positioned on an upstream end of graft 110, a mid-portion of the graft 110, or a downstream portion of the graft 110. Stent elements 120, 121 may represent self-expanding stent elements, and may be formed from a shape-memory alloy such as nitinol, or stent elements 120, 121, may represent balloon expandable stent elements, and may be formed from biocompatible material, such as stainless steel.

Stent graft 100 can be constrained toward a radially collapsed configuration and releasably mounted onto a delivery device such as a catheter assembly. The diameter of the stent graft 100 in the collapsed configuration is small enough for stent graft 100 to be delivered through the vasculature to the treatment area. In the collapsed configuration, stent graft 100 may be carried by or passed through a catheter shaft through the vasculature to the treatment area. In the expanded configuration, the diameter of stent graft 100 can be approximately the same as the vessel to be repaired. In other examples, the diameter of stent graft 100 in the expanded configuration can be slightly larger than the vessel to be treated to provide a traction fit within the vessel.

In various examples, stent graft 100 can comprise a self-expandable device, such as a self-expandable stent graft. Such devices dilate from a radially collapsed configuration to a radially expanded configuration when unrestrained. In other examples, stent graft 100 can comprise a device that is expanded with the assistance of a secondary device such as, for example, a balloon.

In some particular examples, stent graft 100 may be an expandable endoprosthesis used to treat abdominal aortic aneurysms such that stent graft 100 is configured to seal-off the weakened wall of the aorta. Delivery to the treatment site may occur via the femoral or iliac artery in the thigh. The bends and angles of such vasculatures may cause difficulties that are mitigated by the design of stent graft 100.

In various examples, stent graft 100 may comprise a fenestratable portion. In such configurations, stent graft 100 may include a frangible material which may be fenestrated by an endoluminal tool after stent graft 100 has been partially or completely implanted in the vasculature of a patient. Once fenestrated, fenestratable portion may be used, for example, to install branching stent grafts to stent graft 100. Side branch fenestrations allow for branching devices, such as branching stent grafts, to be connected to and in with communication to stent graft 100. Such fenestrations and branching stent grafts may facilitate conforming stent graft 100 and additional branching stent grafts to the anatomy of a patient, such as the thoracic aorta and adjacent vascular branches. In some of such examples, the stent graft 100 may have an internal diameter of the tube of graft 110 of at least 12 millimeters (mm). In the same or different examples, the stent graft 100 may have a length of the tube of graft 110 of at least two times its internal diameter. In one particular example, the internal diameter of the tube of graft 110 may be about 15 mm, and the length of the tube of graft 110 may be about 37 mm. Of course, any dimensions may be selected according to the requirements of the treatment area of the patient. In some example, a surgeon may have a set of stent grafts such as stent graft 100 of various sizes to allow selection of the sizes that best conform to the anatomy of a patient.

In various examples, stent elements 120, 121 and/or graft 110 can comprise a therapeutic coating. In these examples, the interior and/or exterior of the stent component and/or graft member can be coated with, for example, a CD34 antigen. Additionally, any number of drugs or therapeutic agents can be used to coat the graft member, including, for example heparin, sirolimus, paclitaxel, everolimus, ABT-578, mycophenolic acid, tacrolimus, estradiol, oxygen free radical scavenger, biolimus A9, anti-CD34 antibodies, PDGF receptor blockers, MMP-1 receptor blockers, VEGF, G-CSF, HMG-CoA reductase inhibitors, stimulators of iNOS and eNOS, ACE inhibitors, ARBs, doxycycline, and thalidomide, among others.

Stent graft 100 is shown in FIG. 1B in a 90 degree bend without kinking. The expansion of the corrugations on the outside radius of a bend, as shown in FIG. 1B allows stent graft 100 to resist kinking when implanted within a bent portion of a vasculature of a patient, such as the thoracic aorta. By resisting kinking the design of graft 110 may limit the need for stent elements within a middle portion of a graft 110. Stent graft 100 may conform to tortuous vascular anatomy without kinking, while also facilitating tight compaction for intravascular delivery to the treatment site.

Fluid pressure from blood flowing through expanded stent graft 100 may further assist in the prevention of kinking when stent graft 100 is bent as shown in FIG. 1B. The fluid pressure may assist in releasing the stored length of the corrugations of corrugated layer 106 on the outside radius of a bend. For example, stent graft 100 may be configured to resist kinking while experiencing a 90 degree bend with an internal fluid pressure of at least 100 millimeters of mercury (mmHg) such that graft 110 is configured to maintain at least 60% of its cross-sectional area at the apex of the 90 degree bend while experiencing the internal fluid pressure of at least 100 mmHg. 100 mmHg is similar to average human blood pressures, and thus is an approximate representation of pressures experienced by stent graft 100 as implanted within the vasculature of a patient.

FIGS. 2A-2E illustrate example techniques for forming kink resistant stent graft 100 on mandrel 200. Mandrel 200 is a tubular element suitable for supporting receiving various layers of stent graft 100. Mandrel 200 is also suitable for supporting various layers of stent graft 100 during heat treatments, if needed. The use of mandrel 200 is optional as any suitable techniques may be used to form the layers of stent graft 100 as described herein.

Figure 2A:
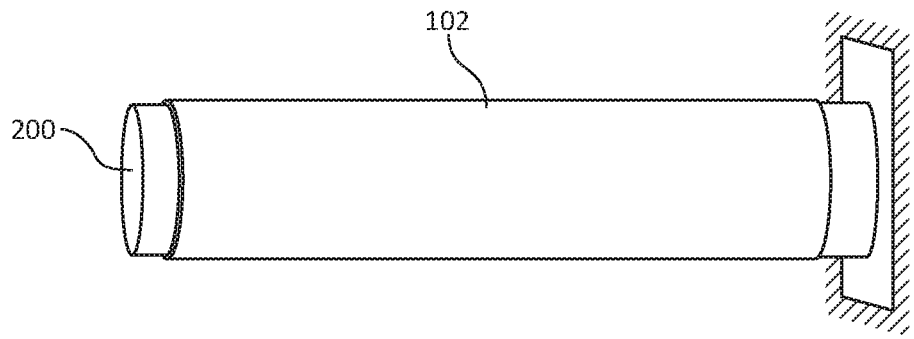
FIGS. 2A-2E illustrate example techniques for forming a kink resistant stent graft on a mandrel.

As shown in FIG. 2A, tubular layer 102 is placed over mandrel 200. For example, tubular layer 102 may be an ePTFE film tube that is then stretched over mandrel 200. The external diameter of mandrel 200 approximates the internal diameter of graft 110. In one particular example, tubular layer 102 may be an ePTFE film tube with an average inner diameter of about 11.5 mm, and mandrel 200 may have an external diameter of about 15 mm. In the same or different examples the external diameter of mandrel 200 and the resulting diameter of the tube may vary over a length of the tube. For example, mandrel 200 may provide a tapered profile with a larger diameter on one end compared to the other end.

Figure 2B:
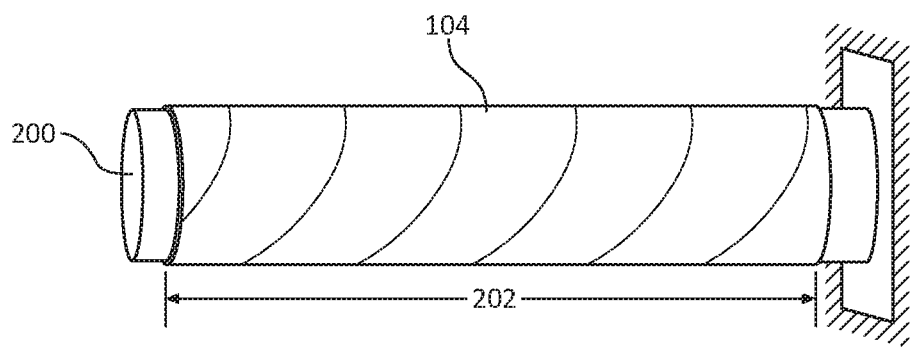

Next, as shown in FIG. 2B, film layer 104 is wrapped over tubular layer 102. After wrapping film layer 104 to form the inner graft layer forming the tube and before scrunching the inner graft layer to form the corrugations in the inner graft layer, heating the wrapped film layer 104 may be heated to set wrapped film layer 104 more permanently into the tube, and/or to bond wrapped film layer 104 with tubular layer 102. As shown, film layer 104 is a helical wrap, although film layer may be any orientation of wrap or combination of orientations, such as longitudinal wraps and cigarette wraps. Tubular layer 102 and film layer 104 form an inner graft layer forming a tube with a central lumen from a first end of the tube to a second end of the tube.

While tubular layer 102 and film layer 104 represent one example of an inner graft layer, any variety of wrapped and/or tubular layers may form an inner graft layer, including only one or more tubular layers, such as tubular layer 102, one or more wrapped layers, such as film layer 104, or any combination of tubular and wrapped layers. Tubular layer 102 and/or film layer 104 may be formed from an ePTFE film or other suitable graft materials. In examples formed from ePTFE, one or both of tubular layer 102 and/or film layer 104 may each have a single layer average wall thickness of no greater than 0.20 nanometers (nm), such as an average wall thickness of no greater than 0.10 nm, such as an average wall thickness of about 0.08 nm.

The tube has a length 202. Optionally, the assembly of tubular layer 102 and film layer 104 may be cooked to bond to one another. Tubular layer 102 and film layer 104 represent one example of an inner graft layer, but any graft material of any number of layers may be used according to desired properties of graft 110.

Figure 2C:
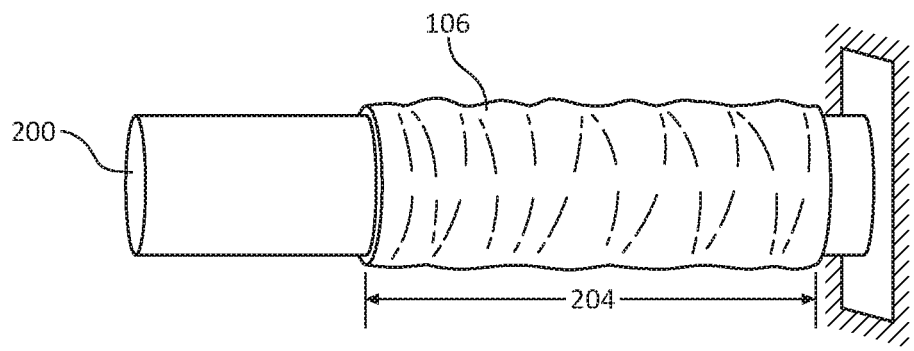

As shown in FIG. 2C, the inner graft layer is scrunched from length 202 to length 204 to form corrugations in the inner graft layer and create corrugated inner graft layer 106, the corrugations providing a stored length of the corrugated inner graft layer 106. The stored length is the ratio of length 204 to length 202. For example, the stored length may be at least twenty-five percent, at least forty percent, or at least fifty percent. In some specific examples, the stored length may be about fifty percent. Generally speaking, kink resistance and wall thickness increases with the stored length, whereas as suppleness and compatibility for intravascular delivery decreases with stored length.

While scrunching an otherwise relatively smooth surfaced tube in one technique to create stored length in a graft layer, other techniques may also be used. For example, a graft layer, such as an inner graft layer in place of tubular layer 102 and film layer 104, may be formed on a mandrel with surface features that provide stored length once the graft layer is removed from the mandrel. As another example, such an inner graft layer may be formed from a material including micro structures including stored length. Examples materials including micro structures including stored length a porous PTFE material with a microstructure including nodes interconnected by fibrils having a bent or wavy appearance, such as that disclosed by U.S. Pat. No. 5,308,664 to House et al., titled, "RAPIDLY RECOVERABLE PTFE AND PROCESS THEREFORE," the entire content of which is incorporated by reference herein for all purposes. As another example, such an inner graft layer may be formed from elastic materials that provide stored length, such as the elastic materials of U.S. Pat. Pub. No. 2014/0135897 by Cully et al., titled, "ELASTIC STENT GRAFT," the entire content of which is also incorporated by reference herein for all purposes. In some examples, such elastic materials may be held in compression by an outer graft layer prior to implantation, releasing the stored length on the outside of the bend upon deployment. In other examples, such elastic materials may be stretched on the outside of the bend upon deployment. Any other techniques for creating stored length in a graft layer may also be used.

In some examples, the corrugations may be relatively consistent along length of a graft. Such examples may provide simplified manufacturability as the graft may be manufactured and then cut to size without regard to varying features along the length of the graft prior to cutting. In other examples, the corrugations may be limited to only some portions of a graft, such as portions which are expected to undergo bending. In the same or different examples, the corrugations themselves may be varied along the length of a graft. For example, corrugations of greater amplitude and/or frequency could be located towards a middle portion of a graft, while corrugations of less amplitude and/or frequency were located beyond the middle portion.

Figure 2D:
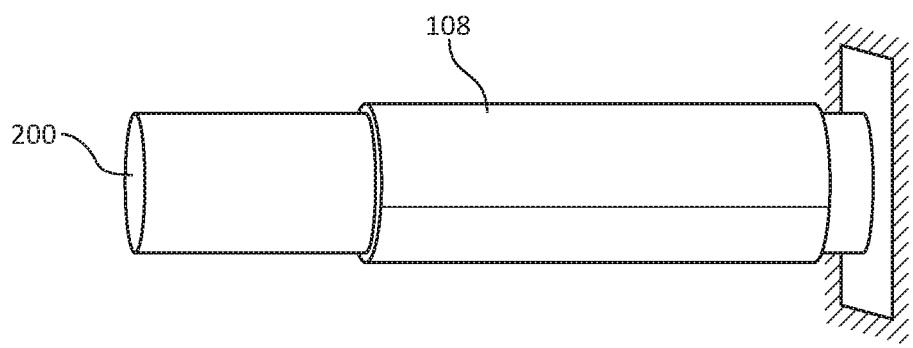

As shown in FIG. 2D, outer graft layer 108 over the corrugated inner graft layer 106 to cover corrugated inner graft layer 106. As shown, outer graft layer 108 is a cigarette wrap, although film layer may be any orientation of wrap or combination of orientations, such as longitudinal wraps and helical wraps. Outer graft layer 108 may be formed from an elastic film, to facilitate stretching on the outside radius during bending of graft 110. For example, outer graft layer 108 may be formed form an ePTFE film or other suitable graft materials.

In some examples, corrugated inner graft layer 106 and outer graft layer 108 may each extend the length of the tube of graft 110. In other examples, the corrugations of inner graft layer 106 may be limited to selected portions of the tube, such as a center portion of the tube. Such examples may provide a smaller collapsed profile for stent graft 100 as the thickness of the corrugations of inner graft layer 106 may not overlap with stent elements 120, 121.

After wrapping outer graft layer 108 over corrugated inner graft layer 106 to cover the corrugated inner graft layer 106, outer graft layer 108 may be bonded to corrugated inner graft layer 106 to form kink resistant graft 110. For example, outer graft layer 108 may be bonded to corrugated inner graft layer 106 by heat treating the assembly of outer graft layer 108 and corrugated inner graft layer 106, for example, by cooking the assembly or by massaging the exterior of outer graft layer 108 with a bonding iron. In other examples, outer graft layer 108 may be adhered to corrugated inner graft layer 106 with a bonding material, such as an adhesive, or by a woven thread or other mechanical connection.

Thus, the construction of kink resistant graft 110 may include two separate heating cycles. A first heating cycle to bond tubular layer 102 and film layer 104 prior to scrunching, and a second heating cycle to bond outer graft layer 108 to corrugated inner graft layer 106. During these heating cycles, the temperature and heating time should be controlled to produce the desired results. In one particular example, the first heating cycle may be between 250 and 350 degrees Celsius for a period of between 30 and 60 minutes. In in the same or different examples, the second heating cycle may be between 180 and 250 degrees Celsius for a period of between 15 and 30 minutes. For example, temperatures that are too high may rearrange the node and fibril structure of PTFE layers. To limit heat exposure to corrugated inner graft layer 106 it may be desirable to select a low melting point material for outer graft layer 108. In some examples, a material for outer graft layer 108 may be a thermoplastic copolymer, such as a thermoplastic copolymer as described in U.S. Pat. No. 8,048,440 to Chang et al., titled, "THERMOPLASTIC FLUOROPOLYMER-COATED MEDICAL DEVICES," the entire content of which is incorporated by reference herein for all purposes.

Figure 2E:
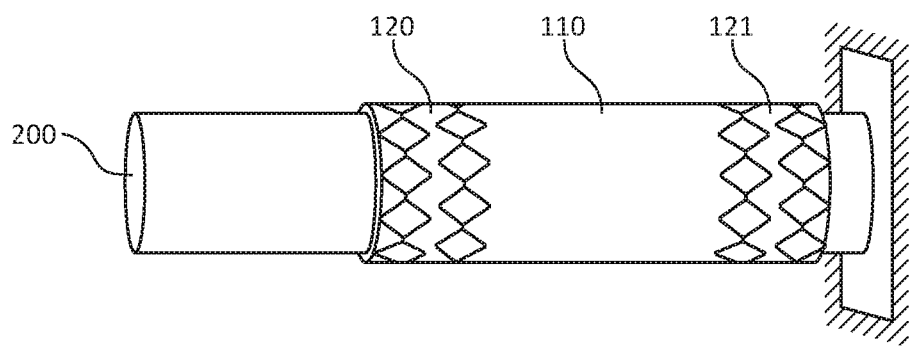

As shown in FIG. 2E, once outer graft layer 108 is adhered to corrugated inner graft layer 106, graft 110 may be cut to a desired length, and stent elements 120, 121 may be added adjacent the ends of the tube of graft 110.

Stent graft 100 may provide one or more advantages as compared to stent grafts including stent elements extending about an entire length of the tube formed by a graft. As one example, by having fewer stent elements, the design of stent graft 100 facilitates lower collapsed profiles for intravascular delivery. In addition as stent elements may cause abrasions in graft material, fewer stent elements also reduce the likelihood that the stent elements wear through the graft material causing failure of the graft. Also, fewer stent elements reduces both collapsed and expanded device stiffness, which may ease implantation through curvatures within a patients vasculature as well as limit the straightening force of the device on a vascular wall once implanted.

Various modifications may be made to the disclosed examples within the spirit of this disclosure, especially in matters of structure, materials, elements, components, shape, size and arrangement of parts including combinations within the principles of the disclosure, to the full extent indicated by the broad, general meaning of the terms in which the appended claims are expressed. For example, while a variety of example configurations are provided, numerous additional configurations for kink resistant grafts including a corrugated graft layer including stored length by way of the corrugations can readily be made within the spirit of this disclosure. To the extent that these various modifications and configurations do not depart from the spirit and scope of the appended claims, they are intended to be encompassed therein.

What is claimed is:
1. A kink resistant stent graft comprising:
   a graft forming a tube with a central lumen extending from a first end of the tube to a second end of the tube, the graft including:
   a corrugated inner graft layer forming at least a middle portion of the tube, wherein corrugations have a greater amplitude toward a middle portion of the graft than corrugations located beyond the middle portion of the graft; and
   an outer graft layer covering the corrugated inner graft layer, the outer graft layer being an elastic film; and
   a stent secured to the graft adjacent the first end of the tube,
   wherein the middle portion of the tube between the first end and the second end does not include a stent.

2. The kink resistant stent graft of claim 1, wherein the corrugated inner graft layer extends from the first end of the tube to the second end of the tube.

3. The kink resistant stent graft of claim 2, wherein the outer graft layer extends from the first end of the tube to the second end of the tube.

4. The kink resistant stent graft of claim 1, wherein the corrugations provide a stored length of the corrugated inner graft layer of at least twenty-five percent, the stored length being a ratio of a first length of the inner graft layer when corrugated to a second length of the inner graft layer when uncorrugated.

5. The kink resistant stent graft of claim 1, wherein the corrugations provide a stored length of the corrugated inner graft layer of at least fifty percent, the stored length being a ratio of a first length of the inner graft layer when corrugated to a second length of the inner graft layer when uncorrugated.

6. The kink resistant stent graft of claim 1, wherein at least one of the corrugated inner graft layer and the outer graft layer are formed from expanded polytetrafluoroethylene (ePTFE) film.

7. The kink resistant stent graft of claim 1, wherein the corrugated inner graft layer and the outer graft layer are bonded to one another.

8. The kink resistant stent graft of claim 1, wherein the graft is configured to resist kinking while experiencing a 90 degree bend with an internal fluid pressure of at least 100 mmHg in that the graft is configured to maintain at least 60% of its cross-sectional area at the apex of the 90 degree bend while experiencing the internal fluid pressure of at least 100 mmHg.

9. The kink resistant stent graft of claim 1, the middle portion having a length of at least twice an external diameter of the tube at the middle portion.

10. The kink resistant stent graft of claim 1, wherein an internal diameter of the tube is at least 12 mm.

11. The kink resistant stent graft of claim 1, wherein the stent is a self-expanding stent.

12. The kink resistant stent graft of claim 1, wherein the stent is a first stent, the kink resistant stent graft further comprising a second stent secured to the graft adjacent the second end of the tube.

13. The stent graft of claim 1, wherein the elastic film of the outer graft layer includes stored longitudinal length that is operable to be longitudinally stretched.

14. The stent graft of claim 1, wherein corrugations have a greater frequency toward the middle portion of the graft than corrugations located beyond the middle portion of the graft.

15. A kink resistant graft device comprising:
a graft forming a tube with a central lumen extending from a first end of the tube to a second end of the tube, the graft including:
a corrugated inner graft layer forming at least a middle portion of the tube, wherein corrugations have a greater frequency toward the middle portion of the graft than corrugations located beyond the middle portion of the graft; and
an outer graft layer covering the corrugated inner graft layer and bonded directly to the corrugated inner graft layer, the outer graft layer being an elastic film; and
a stent secured to the graft adjacent at least one of: the first end of the tube or the second end of the tube,
wherein the middle portion of the tube does not include a stent.

16. The kink resistant graft device of claim 15, wherein the outer graft layer is wrapped helically over the corrugated inner graft layer.

17. The kink resistant graft device of claim 15, wherein the corrugations provide a stored length of the corrugated inner graft layer of at least twenty-five percent, the stored length being a ratio of a first length of the inner graft layer when corrugated to a second length of the inner graft layer when uncorrugated.

18. The kink resistant graft device of claim 15, wherein at least one of the corrugated inner graft layer and the outer graft layer are formed from expanded polytetrafluoroethylene (ePTFE) film.

19. The kink resistant graft device of claim 15, wherein the graft is configured to resist kinking while experiencing a 90 degree bend with an internal fluid pressure of at least 100 mmHg in that the graft is configured to maintain at least 60% of its cross-sectional area at the apex of the 90 degree bend while experiencing the internal fluid pressure of at least 100 mmHg.

20. The kink resistant graft device of claim 15, wherein a middle portion of the tube between the first end and the second end has a length of at least twice an external diameter of the tube at the middle portion.

* * * * *